United States Patent
Ma et al.

(10) Patent No.: US 9,645,053 B2
(45) Date of Patent: May 9, 2017

(54) FLAW DETECTION MACHINE WITH PARALLEL LIFTING FUNCTION, ADAPTED FOR DETECTING FLAW WITHOUT DEMOUNTING WHEELS

(71) Applicant: BEIJING SHEENLINE TECHNOLOGY CO., LTD., Beijing (CN)

(72) Inventors: Jianqun Ma, Beijing (CN); Zhiquan Wang, Beijing (CN); Changyong Rao, Beijing (CN); Ying Tan, Beijing (CN); Houjun Liu, Beijing (CN)

(73) Assignee: BEIJING SHEENLINE GROUP CO., LTD., Beijing (CN)

( * ) Notice: Subject to any disclaimer, the term of this patent is extended or adjusted under 35 U.S.C. 154(b) by 2 days.

(21) Appl. No.: 14/766,099

(22) PCT Filed: Sep. 3, 2014

(86) PCT No.: PCT/CN2014/085810
§ 371 (c)(1),
(2) Date: Aug. 5, 2015

(87) PCT Pub. No.: WO2016/008201
PCT Pub. Date: Jan. 21, 2016

(65) Prior Publication Data
US 2016/0178484 A1 Jun. 23, 2016

(30) Foreign Application Priority Data

Jul. 16, 2014 (CN) .......................... 2014 1 0339320

(51) Int. Cl.
G01M 17/10 (2006.01)
G01M 17/08 (2006.01)
(Continued)

(52) U.S. Cl.
CPC ............ *G01M 17/10* (2013.01); *G01M 17/08* (2013.01); *G01N 29/04* (2013.01); *G01N 29/225* (2013.01); *G01N 2291/2696* (2013.01)

(58) Field of Classification Search
CPC .... G01M 17/08; G01M 17/10; G01N 29/225; G01N 29/04; G01N 2291/2696
See application file for complete search history.

(56) References Cited

U.S. PATENT DOCUMENTS 4,800,748 A    1/1989 Fischer et al.

FOREIGN PATENT DOCUMENTS

CN    2745057 Y    12/2005
CN    201697897 U  * 1/2011
(Continued)

OTHER PUBLICATIONS

English translation for CN201697897.*
(Continued)

Primary Examiner — Paul West
Assistant Examiner — Xin Zhong
(74) Attorney, Agent, or Firm — Oliff PLC

(57) ABSTRACT

A flaw detection machine with parallel lifting function, adapted for detecting flaw without demounting wheels, includes a trolley, slidable along steel rail, a base frame, a jacking apparatus and a tread flaw detecting device provided on the trolley, a first jacking mechanism for driving the jacking apparatus to move up and down, a second jacking mechanism for driving the tread flaw detecting device to move up and down, the tread flaw detecting device has a vertical frame, a tread probe manipulator provided at an upper end of the vertical frame, a tread probe frame provided on the tread probe manipulator, and the jacking apparatus is mounted on the vertical frame and able to slide up and down along an inner side wall of the vertical frame.

15 Claims, 3 Drawing Sheets

(51) Int. Cl.
*G01N 29/04* (2006.01)
*G01N 29/22* (2006.01)

(56) References Cited

FOREIGN PATENT DOCUMENTS

| CN | 102175774 A | 9/2011 |
| CN | 102269660 A | 12/2011 |
| CN | 203455316 U | 2/2014 |
| CN | 203965390 U | 11/2014 |

OTHER PUBLICATIONS

Dec. 30, 2015 Office Action issued in Chinese Patent Application No. 201410339320.X.
Jan. 6, 2015 Written Opinion issued in International Patent Application No. PCT/CN2014/085810.
Jan. 6, 2015 International Search Report issued in International Patent Application No. PCT/CN2014/085810.

* cited by examiner

FLAW DETECTION MACHINE WITH PARALLEL LIFTING FUNCTION, ADAPTED FOR DETECTING FLAW WITHOUT DEMOUNTING WHEELS

TECHNICAL FIELD

The present invention relates to the technical field of railway vehicle wheels detection, especially relates to a flaw detection machine with parallel lifting function, adapted for detecting flaw without demounting wheels.

BACKGROUND OF THE INVENTION

The railway vehicle wheels are subjected to large alternating stress in operation, a crack may be formed therein, and this may cause a safety hazard, thus, the wheels should be ultrasonic detected regularly. In recent years, a kind of ultrasonic flaw detection equipment adapted for detecting flaw without demounting wheels is developed, that is, the wheel is not disassembled, and when detecting flaw, the wheels can be normally installed on the vehicle. The basic form of this kind of flaw detection equipment is that vehicles are parked on the special steel rails for aerial rail bridge; a flaw detection machine rail which is parallel to steel rails is provided in the trench under the rail bridge; the flaw detection machine is slidable along the rail and can stop at the bottom of each vehicle wheel; then the jacking frame of flaw detection machine is lifted, so that the wheel is lifted away from the steel rail, and the wheel is rotated, then felloe probe manipulator on the jacking frame detects the felloe; then the vertical rail on jacking frame is further lifted, and the tread probe manipulator on the jacking frame leads ultrasonic probe holder to abut against the wheel, in order to detects the flaw of the wheels.

The lifting of jacking frame and vertical guide rail of the traditional flaw detection machine for rail vehicle wheel is a serial movement (the vertical guide rail is provided on the jacking frame, and the vertical guide rail is lifted along with the jacking frame), the height of the vertical guide rail is correlated with the height of the top wheel frame, in the narrow space at the bottom of the wheel, this relationship between the vertical guide rail and the jacking frame causes that the tread probe manipulator can not be moved vertical to the steel rail from one side of the wheel to the other side above the top wheel frame, and in order to realize the detection on the wheel, the manipulator must carry on complicated movement, the operation is very complicated and time-consuming, and the efficiency is lower. In the actual operation, this kind of tread probe manipulator is easy to collide with machinery on the bottom of vehicles, and at the same time, it cannot be used on some kinds of vehicles, these serious defects are not suitable for high-speed railway, which may be of high tempo and have different types of vehicles. Therefore, a high efficiency flaw detection machine which is suitable for detecting flaw without demounting wheels is needed.

SUMMARY OF THE INVENTION

The technical problem to be solved by the present invention is that when the tread probe manipulator of the flaw detection machine adapted for detecting flaw without demounting railway vehicle wheels in the prior art moves from one side to the other side, it needs complicated action transformation to be achieved, which leads to problems of complicated operation and low efficiency. Thus, one objective of the present invention is to provide a flaw detection machine with parallel lifting function, adapted for detecting flaw without demounting wheels, which is simple to operate and more efficient and safer, and the tread probe manipulator can flexibly move from one side of the detected wheel to the other side.

In order to realize the above objective, the present invention a flaw detection machine with parallel lifting function, adapted for detecting flaw without demounting wheels, comprising a trolley, slidable along two steel rails, between which it is provided, a base frame, provided on said trolley, a jacking apparatus for jacking wheels, with a felloe probe holder provided thereon, a tread flaw detecting device for detecting the flaw of the treads of the wheels, a first jacking mechanism for driving said jacking apparatus to move up and down, a second jacking mechanism for driving said tread flaw detecting device to move up and down, said tread flaw detecting device comprises a vertical frame, mounted on said base frame and able to slide up and down along an inner side wall of said base frame, a tread probe manipulator, provided at an upper end of said vertical frame and slidable along the length direction of said steel rail and a tread probe frame, provided on said tread probe manipulator, and said jacking apparatus is mounted on said vertical frame and able to slide up and down along an inner side wall of said vertical frame.

Said vertical frame being mounted on said base frame and able to slide up and down along said inner side wall of said base frame is realized, by providing a linear sliding pair between said vertical frame and said base frame.

Said tread probe manipulator being mounted on said vertical frame and slidable along a direction parallel with that of said steel rail is realized, by providing a linear sliding pair between a top of said vertical frame and a bottom of said tread probe manipulator.

Said jacking apparatus being slidably mounted on said vertical frame is realized by providing a linear sliding pair between said inner side wall of said vertical frame and an end of said jacking apparatus.

Said base frame is a rectangular base formed by a bottom surface and four side walls; a first guide rail or a guide channel extending along the up and down direction is formed on the inner surface of two opposite side walls, a lower end of said vertical frame is a first rectangular frame formed by four side walls, which is adapted for being inserted into said first rectangular base, and both ends of the first rectangular frame are formed with a first guide channel coordinating with said first guide rail, or a first guide rail coordinating with a first guide channel; an upper end of said vertical frame is formed by said first guide channels or first guide rails formed on both ends of the first rectangular frame, which extend upwardly; a vertical guide rail extending along the length direction of said steel rail is arranged on an upper end of said first guide channels or first guide rails on the both ends, said tread probe manipulator is slidably arranged on said vertical guide rail through a longitudinal guide channel on the bottom.

Said first guide channels or first guide rails are formed on two opposite side walls of said frame base, which are perpendicular with said steel rails, two opposite side walls of said frame base, which are parallel with said steel rails, are respectively provided with a first mounting hole for a tool to be inserted therein; two opposite side walls of said vertical frame, which are parallel to said steel rails, are respectively provided with a second mounting hole for a tool to be inserted therein.

Said jacking apparatus comprises a jacking frame, slidable along the inner side wall of said vertical frame, a jacking structure for jacking wheels, provided on both sides of said jacking frame, and a felloe probe holder for detecting the flaw of the felloe, and said jacking frame is provided below the path of said tread probe manipulator moving along the length direction of said steel rails.

Said jacking frame is a second rectangular frame formed by four side walls, second guide rails or second guide channels which extend along up and down direction are formed on an inner side of said vertical frame; guide channels or guide rails, which coordinate with said second guide rails or guide channels are formed on an outer side of the end of said second rectangular frame.

Said jacking structure comprises a slide bar, vertically fixed on said side wall of said jacking frame, which is parallel with said steel rails; both ends of said slide bar extend out of said side wall of said jacking frame; a bracket is sleeved on one end of said slide bar, which extends out of said side wall; a roller is provided on an upper end of said bracket; a driving device is provided on at least one of two said rollers provided on the same side as said jacking frame; a bracket swing mechanism is connected with the lower ends of both said brackets provided on the same side as said jacking frame.

Said bracket swing mechanism is an electric cylinder or an oil cylinder or an air cylinder, and both ends of said electric cylinder or oil cylinder or air cylinder are respectively fixed on the lower ends of two said brackets.

Said bracket is V-shaped, and two said brackets have openings on the same side as said jacking frame are arranged oppositely.

A hook device for hanging said jacking frame on said steel rail is provided between the side walls of said bracket and said jacking frame; said hook device comprises a hook beam, slidably sleeved on said slide bar, a telescopic mechanism for driving said hook beam to stretch out and draw back along the vertical direction of said steel rail, provided at the inner side of said jacking frame; a hook portion, provided at a free end of said hook beam which extends towards one side of said steel rails and connects with said steel rails in a lapped manner.

A flaw detecting device for the felloe is provided between two said slide bars; said flaw detecting device comprises a felloe probe manipulator fixed on the outer wall of said jacking frame, and a felloe probe holder for mounting the detection probe, provided at an end of said felloe probe manipulator.

Said first jacking mechanism, said second jacking mechanism and said telescopic mechanism are an electric cylinder or oil cylinder or air cylinder.

Two said tread probe frames, respectively provided at both ends of said tread probe manipulator.

The flaw detection machine with parallel lifting function, adapted for detecting flaw without demounting wheels in the present invention has the following advantages:

1. in the flaw detection machine with parallel lifting function, adapted for detecting flaw without demounting wheels of the present invention, since the vertical frame for mounting tread probe and the jacking apparatus for jacking wheels are lifting independently base on the trolley, the height between the two can be adjusted according to needs, and the tread probe manipulator is provided above the jacking frame, when moving the tread probe manipulator, it will not pass through the jacking frame, and the lifting height of the tread probe manipulator can be discretionarily adjusted, therefore the tread probe manipulator can be conveniently moved from one side of the wheel to the other side above the jacking frame, which simplifies the operation, enhances the detection efficiency and has a better working stability and safety.

2. The base frame, the vertical frame and the jacking frame of the flaw detection machine in the present invention are designed into a rectangular structure, and this kind of structure has a better ability of bearing the external force, the operation process is more stable and the positioning accuracy is higher.

3. Two opposite side walls of the frame base of the flaw detection machine in the present invention, which are parallel with said steel rails, are respectively provided with a first mounting hole for a tool to be inserted therein, two opposite side walls of the vertical frame, which are parallel to said steel rails, are respectively provided with a second mounting hole for a tool to be inserted therein, the two mounting holes are in the shape of rectangular, and an transition in the form of an circular arc is formed at each corner, by providing mounting holes, the assembly and the maintenance of the whole flaw detection machine become easier, at the same time, the area of plank is reduced, which may reduce the weight of the whole flaw detection machine and also reduce the fabricating cost.

4. A hook device for hanging the jacking frame on the steel rail is provided on the slide bar of the flaw detection machine in the present invention, and a telescopic mechanism is provided between the hook devices at the both sides, the telescopic mechanism is adapt for driving the hook beam at the both sides to move close to or away from steel rail, and the hook beam is connected to the bracket along the axial direction by linkage member; before lifting the wheel, the jacking frame is raised to a little higher than the steel rail, then the telescopic mechanism is operable to drive the hooks at the both sides to placed on the steel rails on the both sides, after that the bracket swing mechanism extends to the both sides for lifting the two brackets, until the wheel is separated from the surface of the steel rail, then the weight of the whole wheel is passed to the steel rail through the hook beam, thereby avoiding the damage to the trolley.

5. The flaw detecting devices for the felloe are provided at the both sides of the jacking frame of the flaw detection machine in the present invention, when the jacking frame lifting the two wheels on the same shaft, two felloe probes can detect the flaw of felloe of two wheels at the same time, and then the efficiency of detection can be enhanced.

6. In the present invention, two tread probe frames are respectively provided at both ends of said tread probe manipulator; when detecting flaw, two felloe probes can detect the two wheels on the same shaft at the same time, and then the efficiency of detection can be enhanced.

BRIEF DESCRIPTION OF THE DRAWINGS

In order to make the invention easier to be clearly understood, the invention will be described in greater detail with references to the embodiments and the appended drawings, wherein.

Wherein,

1—trolley, 2—vertical frame, 20—first guide rail, 21—second mounting hole, 3—base frame, 31—first mounting hole, 4—felloe probe manipulator, 5—second jacking mechanism, 6—felloe probe holder, 7—jacking frame, 70—second guide rail, 8—vertical guide rail, 9—first jacking mechanism, 10—tread probe manipulator, 11—tread probe frame, 12—first guide channel, 13—second guide channel, 14—roller, 15—bracket, 16—slide bar, 17—telescopic mechanism, 18—bracket swing mechanism, 19—hook beam, 190—hook portion.

DETAILED DESCRIPTION OF THE PREFERRED EMBODIMENTS

Figure 1:
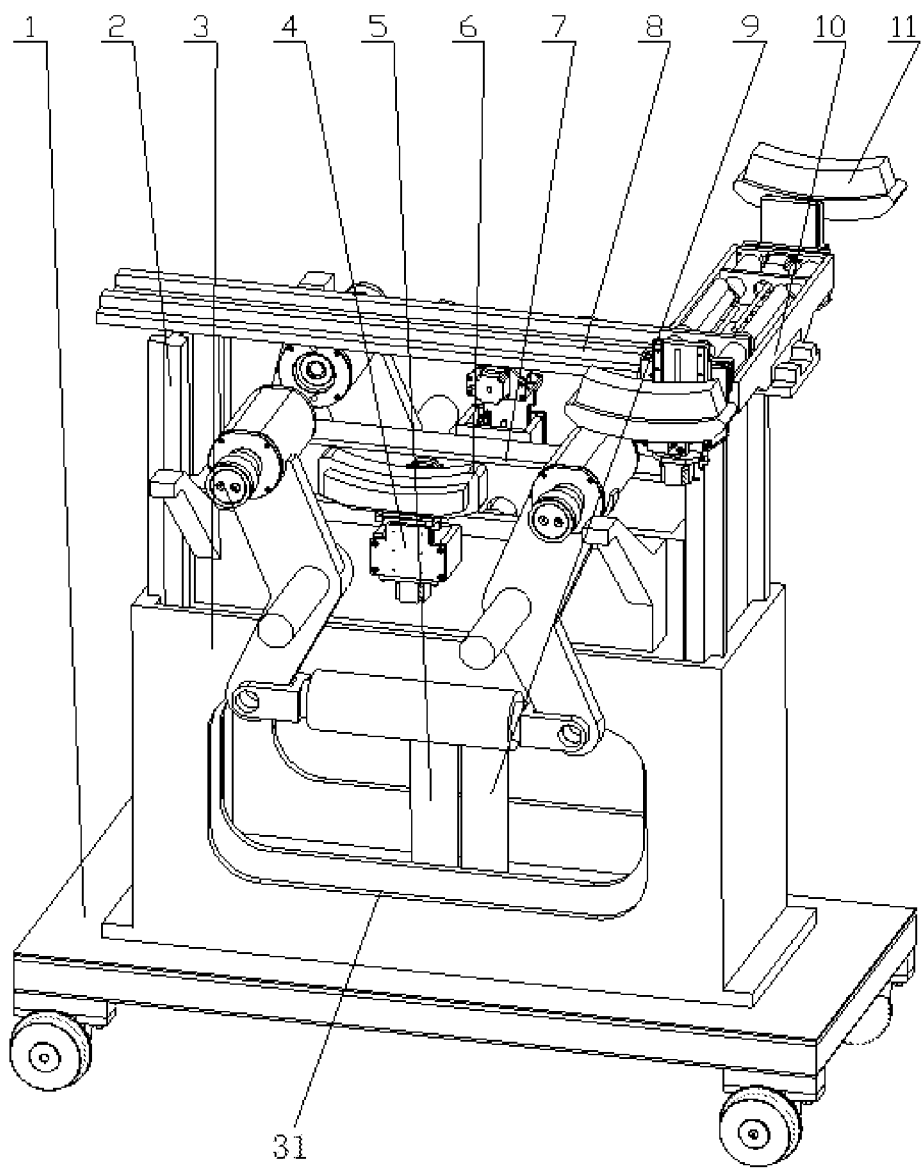
FIG. 1 is a structure schematic view of the flaw detection machine in the present invention.
Figure 4:
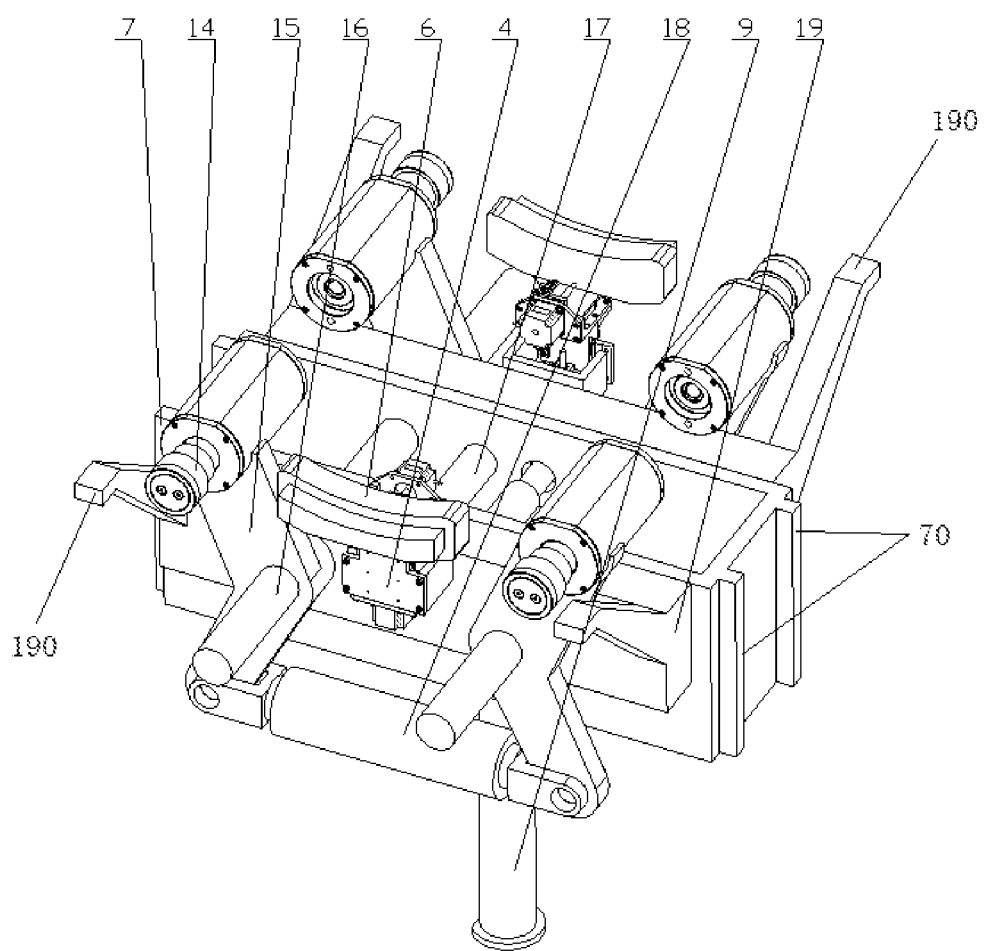
FIG. 4 is a structure schematic view of the jacking frame of the flaw detection machine in the present invention.

As shown in FIG. 1 and FIG. 4, the flaw detection machine with parallel lifting function, adapted for detecting flaw without demounting wheels in the present embodiment, comprises a trolley 1, slidable along two steel rails, between which it is provided, a base frame 3, provided on the trolley 1; a jacking apparatus for jacking wheels, with a felloe probe holder 6 provided thereon; a tread flaw detecting device for detecting the flaw of the treads of the wheels; a first jacking mechanism 9 for driving the jacking apparatus to move up and down; a second jacking mechanism 5 for driving the tread flaw detecting device to move up and down; the tread flaw detecting device comprises a vertical frame 2, mounted on the base frame 3 and able to slide up and down along an inner side wall of the base frame 3, a tread probe manipulator 10, provided at an upper end of the vertical frame 2 and slidable along the length direction of the steel rail and a tread probe frame 11 provided on the tread probe manipulator 10, a flaw probe is provided on the tread probe frame 11; and the jacking apparatus is mounted on the vertical frame 2 and able to slide up and down along an inner side wall of the vertical frame, a felloe flaw detecting device is provided on the jacking apparatus. Since the vertical frame for mounting tread probe and the jacking apparatus for jacking wheels are lifted independently based on the trolley, the height between the two can be adjusted as needed, that is, the vertical frame can be adjusted to stay higher than the jacking apparatus, and the jacking apparatus can also be adjusted to stay higher than the vertical frame, and the tread probe manipulator is provided at an upper end of the vertical frame and above the jacking frame, when moving the tread probe manipulator, it will not pass through the jacking frame, and the lifting height of the tread probe manipulator can be discretionarily adjusted, therefore the tread probe manipulator can conveniently move from one side of the wheel to the other side above the jacking frame, which simplifies the operation, enhance the detection efficiency with better working stability and safety. In the present invention, the tread flaw detecting device and the felloe flaw detecting device are driven by different jacking mechanism, the two detecting device can move up and down independently without interference with each other, therefore, the tread flaw detecting device can conveniently move from one side of the wheel to the other side in a limited space under the vehicle, without complex operation of the tread flaw detecting device, which provides higher flexibility.

In the present embodiment, the vertical frame 2 is mounted on the base frame and able to slide up and down along the inner side wall of the base frame 3, by providing a linear sliding pair between the vertical frame 2 and the base frame 3. Since the linear sliding pair is formed by two sliding rail structures coordinating with each other, therefore, the base frame 3 can be provided with guide rail or guide channel, correspondingly, the vertical frame 2 is provided with a corresponding guide channel or a guide rail. And since the structure of the linear sliding pair limits the movement of vertical frame 2 and only allow it to move vertically, the flaw detection machine in the present embodiment has a more stable operation state.

In the present embodiment, the tread probe manipulator 10 being mounted on the vertical frame 2 and slidable along a direction parallel with that of the steel rail is realized, by providing a linear sliding pair between a top of the vertical frame 2 and a bottom of the tread probe manipulator 10.

In the present embodiment, the jacking apparatus being slidably mounted on the vertical frame 2 is realized by providing a linear sliding pair between the inner side wall of the vertical frame 2 and an end of the jacking apparatus. Similarly, a guide rail or a guide channel can be provided at the coordination position inside the vertical frame 2, of course, the above mentioned coordination of guide rail and guide channel may not necessarily need to provide guide rail and guide channel respectively on two coordination members, it can also be two parallel rails on the coordination surface of two members, and make two rails on one of the members exactly located in the gap between rails on the other member, and then realize the slidable coordination of the rails.

Figure 2:
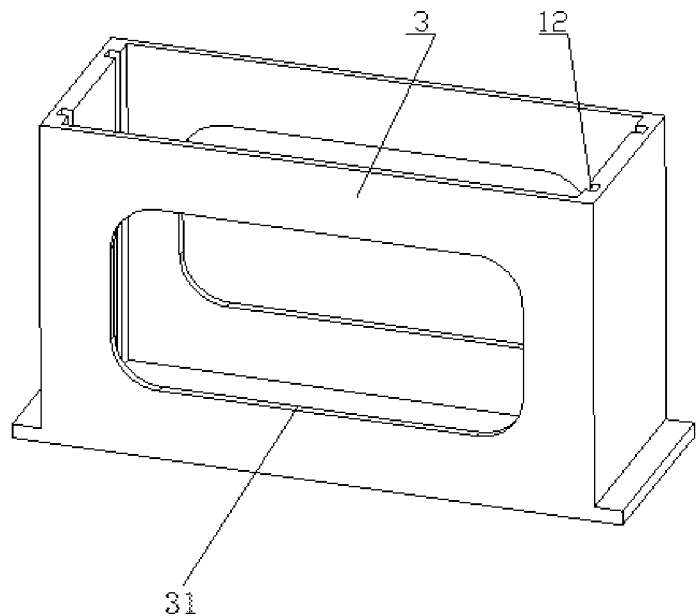
FIG. 2 is a structure schematic view of the base frame of the flaw detection machine in the present invention.
Figure 3:
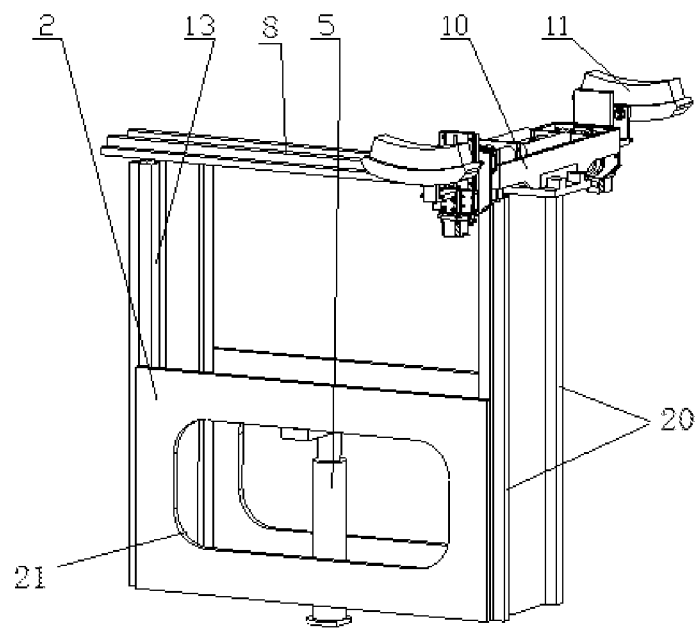
FIG. 3 is a structure schematic view of the vertical frame of the flaw detection machine in the present invention.

Specifically, the present embodiment relates to a preferred setting method, the base frame 3 is a rectangular base formed by a bottom surface and four side walls, see FIG. 2, a guide channel 12 extending along the up and down direction is formed on the inner surface of two side walls which are vertical to the steel rail, a lower end of the vertical frame 2 is a first rectangular frame formed by four side walls, see FIG. 3, which is adapted for being inserted into the first rectangular base, and both ends two side walls which are vertical to the steel rail of the first rectangular frame are formed with a first guide rail 20 coordinating with a first guide channel 12, an upper end of the vertical frame 2 is formed by the first guide rails 20 formed on both ends of the first rectangular frame, which extends upwardly; a vertical guide rail 8 extending along the length direction of the steel rail is arranged on an upper end of the first guide rails 20 on the both ends, the tread probe manipulator 10 is slidably arranged on the vertical guide rail through a longitudinal guide channel on the bottom. In order to enhance the sliding accuracy, the cross section of the longitudinal guide channel on the bottom of the tread probe manipulator 10 is a rectangular structure.

As shown in FIG. 2 and FIG. 3, two opposite side walls of the frame base 3 of the present embodiment, which are parallel with the steel rails, are respectively provided with a first mounting hole 31 for a tool to be inserted therein; two opposite side walls of the vertical frame 2, which are parallel to the steel rails, are respectively provided with a second mounting hole 21 for a tool to be inserted therein. The two mounting holes are in the shape of rectangular, and a transition in the form of an circular arc is formed at each corner. By providing mounting holes, the assembly and the maintenance of the whole flaw detection machine become more easily, at the same time, the area of plank is reduced, which may reduce the weight of the whole flaw detection machine and also reduce the fabricating cost.

Of course, the second mounting hole 21 and the first mounting hole 31 can also be arranged in other shapes, such as circular, trapezoid, etc, a plurality of mounting holes may also be provided on the corresponding wall of the base frame 3 and the tread probe frame.

As shown in FIG. 1 and FIG. 4, the jacking apparatus of the present embodiment comprises a jacking frame 7 slidable up and down along the inner side wall of the vertical frame 2, a jacking structure for jacking wheels, which is provided on both sides of the jacking frame 7, and a felloe probe holder 6 for detecting the flaw of the felloe, which has a probe provided thereon; in addition, the jacking frame 7 is provided below the path of the tread probe manipulator 10 moving along the length direction of the steel rails.

In the present embodiment, the jacking frame 7 is a second rectangular frame formed by four side walls, second guide channels 13 which extend along up and down direction are formed on an inner side of the vertical frame 2, the second guide rails 70, which coordinate with the second guide channels 13 are formed on an outer side of the end of the second rectangular frame. In the present embodiment, since the guide rail and the guide channel on the vertical frame 2 and the jacking frame 7 coordinate with each other, the guide rail or the guide channel can be provided either on the vertical frame 2 or on the jacking frame 7, which can be determined according to the actual situation.

As shown in FIG. 4, the jacking structure comprises a slide bar 16, vertically fixed on the side wall of the jacking frame 7, which is parallel with the steel rails, both ends of the slide bar 16 extend out of the side wall of the jacking frame 7, a bracket 15 is sleeved on one end of the slide bar 16, which extends out of the side wall; a roller 14 is provided on an upper end of the bracket 15, a driving device is provided on one of two rollers 14 provided on the same side of the jacking frame 7, if the power of the motor is small, the driving device can be respectively provided on both rollers 14, the driving device drives the rollers to rotate, and then drives the wheel to rotate, the driving device can be an electric motor, a fluid motor, etc.

In the present embodiment, a bracket swing mechanism 18 is connected with the lower ends of both the brackets 15 provided on the same side as that of the jacking frame 7, the bracket swing mechanism 18 may be an electric cylinder or an oil cylinder or an air cylinder, and both ends of the electric cylinder or oil cylinder or air cylinder are respectively fixed on the lower ends of two the brackets 15. When the bracket swing mechanism 18 stretches out towards both sides, the distance between two brackets is reduced, then the wheel roller is driven to move upwards and gradually separated from the surface of the steel rail.

In the present embodiment, the bracket 15 is V-shaped, and two the brackets 15 have openings on the same side as that of the jacking frame 7 and are arranged oppositely. Comparing with a rod shaped bracket having the same length, the V-shaped bracket can lift the wheel to a higher position, which is better for detecting flaw.

As shown in FIG. 1 and FIG. 4, a hook device for hanging the jacking frame 7 on the steel rail is provided between the bracket 15 and the side walls of the jacking frame 7, the hook device comprises a hook beam 19, slidably sleeved on the slide bar 16, a telescopic mechanism 17 provided at the inner side of the jacking frame 7 for driving the hook beam 19 to stretch out and draw back in vertical direction along the steel rail, the telescopic mechanism 17 is adapted for driving the hook beam 19 at the both sides to move close to or away from steel rail, and the hook beam 19 is connected to the bracket 15 by a linkage member so to allow both to move axially in the same direction on the slide bar 16; when the telescopic mechanism 17 drives the hook beam 19 to move axially in the same direction of the slide bar 16, the bracket 15 may move along with the hook beam 19; a hook portion 190 is provided at a free end of the hook beam 19, which extends towards one side of the steel rails and is connected with the steel rails in a lapped manner. Before the wheel is lifted, the jacking frame 7 is operable to be raised to a position that is a little higher than the steel rail by driving the first jacking mechanism 9, then the telescopic mechanism 17 is operable to drive the hook beams 19 and the brackets 15 at the both sides to move towards outside, when the hook portions 190 on the both sides are placed on two steel rails, the bracket swing mechanism 18 is operable to stretch to the both sides to lift the two rollers 14 on the two brackets, until the wheel is separated from the surface of the steel rail, then the weight of the whole wheel is passed to the steel rail through the hook beam 19, thereby avoiding the damage to the trolley.

In the present embodiment, the flaw detecting device for the felloe is provided between two slide bars 16, the flaw detecting device comprises a felloe probe manipulator 4 fixed on the outer wall of the jacking frame 7, and a felloe probe holder 6 for mounting the detection probe, provided at an end of the felloe probe manipulator 4. Since the felloe probe manipulator 4 has two felloe probe holders 6 respectively provided at both sides thereof, the two felloe probe holders 6 are operable to detect the flaw of felloe of two wheels at the same time, and then the efficiency of detection is enhanced.

In the present embodiment, the first jacking mechanism 9, the second jacking mechanism 5 and the telescopic mechanism 17 may be an electric cylinder or an oil cylinder or an air cylinder.

In the present embodiment, the tread probe manipulator 10 may have two the tread probe frames 11 respectively provided at both ends thereof. By providing two tread probe frames, the felloe of two wheels can be detected at the same time, and then the efficiency of detection is enhanced.

The working process of the flaw detection machine of the present invention is described in details as bellow:

When the flaw detection machine of the present invention is working, the vehicle is parked on the steel rails of the aerial rail bridge. The structure of rail vehicle is that a bogie is provided under the carriage, and generally, one bogie is provided with two vehicle axles, both ends of each axle are provided with wheels, an outer circumference of the wheel is called tread, which contacts with the surface of the steel rail, a flange which has a outer diameter longer than that of the tread is provided inside the tread, the outer side of the flange, which is the surface connected to the tread, contacts with the inner side of the steel rail, which has a guiding function, the inner surface of the flange is called felloe.

When detecting flaw, the trolley 1 placed in a pit is moved to a position under an axle of the vehicle, the vertical frame 2 is driven by the second jacking mechanism 5 and lifted along the first guide channel 12 on the base frame, then the jacking frame is driven by the first jacking mechanism and lifted along the second guide channel 13; two parallel slide bars 16 which are vertical to steel rails are provided at the middle portion of the jacking frame 7, two hook beams 19 provided at both sides of the jacking frame 7 are slidably sleeved on the slide bars 16, after the jacking frame is lifted, the two hook beams 19 are driven by the telescopic mechanism 17 to move outwards at the same time, the hooks on the hook beam 19 are placed on two steel rails; a pair of brackets 15 are provided at the outer side of each hook beam 19, the brackets 15 are also slidably sleeved on the slide bars 16, a roller 14 is provided on the upper end of each bracket 15, the brackets 15 moves along with the hook beam 19, when the hook is placed on steel rail, the rollers 14 on brackets 15 on the both sides are moved to the position under the flanges of the two wheels, then the brackets 15 are driven by the bracket swing mechanism to swing towards the wheel, the roller 14 lifts the wheel, until the wheel is separated from the surface of the steel rail, and drives the wheel to rotate; then the tread probe manipulator 10 on the vertical frame 2 allows two tread probe frames 11 to abut against the treads of two wheels, and at the same time, the felloe probe manipulator 4 mounted on two hook beams 19 allow the two felloe probe holders 6 to abut against the felloes of two wheels, thus, the two wheels on the same axle can be detected at the same time. After detecting flaw, every probe frame is retracted, the brackets 15 swing in a reverse direction, the wheel is placed on the steel rail, the hook beam 19 and the bracket 15 are retracted, the jacking frame goes back to the initial position, the vertical frame is lowered to avoid the obstacle at the lower portion of the bogie, so that the tread probe manipulator is able to be moved to the other side of the wheel along the vertical guide rail 8 for the purpose of detecting flaw on either side of the wheel.

The above mentioned embodiments are for a clear description of technical specifications on the present invention, which do not constitute undue limitation of the present invention. It is obvious to the skilled person in the art that, various modifications could be derived without departing from the spirits and the effects of the invention, the modifications or alternations derived thereof are still included in the protection scope of the present invention.

The invention claimed is:

1. A flaw detection machine with parallel lifting function, adapted for detecting flaw without demounting wheels, comprising
    a trolley, slidable along two steel rails, between which it is provided,
    a base frame, provided on said trolley,
    a jacking apparatus for jacking wheels, with a felloe probe holder provided thereon,
    a tread flaw detecting device for detecting the flaw of the treads of the wheels,
    a first jacking mechanism for driving said jacking apparatus to move up and down,
    a second jacking mechanism for driving said tread flaw detecting device to move up and down,
    wherein, said tread flaw detecting device comprises
    a vertical frame, mounted on said base frame and able to slide up and down along an inner side wall of said base frame,
    a tread probe manipulator, provided at an upper end of said vertical frame and slidable along the length direction of said steel rail, and
    a tread probe frame, provided on said tread probe manipulator,
    said jacking apparatus is mounted on said vertical frame and able to slide up and down along an inner side wall of said vertical frame, and
    the first jacking mechanism and the second jacking mechanism are supported by the trolley and respectively drive the jacking apparatus and the vertical frame to move up and down relative to the trolley independently without interference with each other.

2. The flaw detection machine of claim 1, wherein, said vertical frame being mounted on said base frame and able to slide up and down along said inner side wall of said base frame is realized, by providing a linear sliding pair between said vertical frame and said base frame.

3. The flaw detection machine of claim 2, wherein, said tread probe manipulator being mounted on said vertical frame and slidable along a direction parallel with that of said steel rail is realized, by providing a linear sliding pair between a top of said vertical frame and a bottom of said tread probe manipulator.

4. The flaw detection machine of claim 3, wherein, said jacking apparatus being slidably mounted on said vertical frame is realized by providing a linear sliding pair between said inner side wall of said vertical frame and an end of said jacking apparatus.

5. The flaw detection machine of claim 1, wherein, said base frame is a rectangular base formed by a bottom surface and four side walls;
    a first guide rail or a guide channel extending along the up and down direction is formed on the inner surface of two opposite side walls,
    a lower end of said vertical frame is a first rectangular frame formed by four side walls, which is adapted for being inserted into said first rectangular base, and
    both ends of the first rectangular frame are formed with a first guide channel coordinating with said first guide rail, or a first guide rail coordinating with a first guide channel;
    an upper end of said vertical frame is formed by said first guide channels or first guide rails formed on both ends of the first rectangular frame, which extend upwardly;
    a vertical guide rail extending along the length direction of said steel rail is arranged on an upper end of said first guide channels or first guide rails on the both ends,
    said tread probe manipulator is slidably arranged on said vertical guide rail through a longitudinal guide channel on the bottom.

6. The flaw detection machine of claim 5, wherein, said first guide channels or first guide rails are formed on two opposite side walls of said frame base, which are perpendicular with said steel rails,
    two opposite side walls of said frame base, which are parallel with said steel rails, are respectively provided with a first mounting hole for a tool to be inserted therein;
    two opposite side walls of said vertical frame, which are parallel to said steel rails, are respectively provided with a second mounting hole for a tool to be inserted therein.

7. The flaw detection machine of claim 1, wherein, said jacking apparatus comprises
    a jacking frame, slidable along the inner side wall of said vertical frame,
    a jacking structure for jacking wheels, provided on both sides of said jacking frame, and
    a felloe probe holder for detecting the flaw of the felloe, and
    said jacking frame is provided below the path of said tread probe manipulator moving along the length direction of said steel rails.

8. The flaw detection machine of claim 7, wherein, said jacking frame is a second rectangular frame formed by four side walls,
    second guide rails or second guide channels which extend along up and down direction are formed on an inner side of said vertical frame;
    guide channels or guide rails, which coordinate with said second guide rails or guide channels are formed on an outer side of the end of said second rectangular frame.

9. The flaw detection machine of claim 8, wherein, said jacking structure comprises a slide bar, vertically fixed on said side wall of said jacking frame, which is parallel with said steel rails;

both ends of said slide bar extend out of said side wall of said jacking frame;
a bracket is sleeved on one end of said slide bar, which extends out of said side wall;
a roller is provided on an upper end of said bracket;
a driving device is provided on at least one of two said rollers provided on the same side as said jacking frame;
a bracket swing mechanism is connected with the lower ends of both said brackets provided on the same side as said jacking frame.

10. The flaw detection machine of claim 9, wherein,
said bracket swing mechanism is an electric cylinder or an oil cylinder or an air cylinder, and both ends of said electric cylinder or oil cylinder or air cylinder are respectively fixed on the lower ends of two said brackets.

11. The flaw detection machine of claim 10, wherein,
said bracket is V-shaped, and two said brackets have openings on the same side as said jacking frame are arranged oppositely.

12. The flaw detection machine of claim 11, wherein,
a hook device for hanging said jacking frame on said steel rail is provided between the side walls of said bracket and said jacking frame;
said hook device comprises
a hook beam, slidably sleeved on said slide bar,
a telescopic mechanism for driving said hook beam to stretch out and draw back along the vertical direction of said steel rail, provided at the inner side of said jacking frame;
a hook portion, provided at a free end of said hook beam which extends towards one side of said steel rails and connects with said steel rails in a lapped manner.

13. The flaw detection machine of claim 12, further comprising a flaw detecting device for the felloe, which is provided between two said slide bars; said flaw detecting device comprises a felloe probe manipulator fixed on the outer wall of said jacking frame, and
a felloe probe holder for mounting the detection probe, provided at one end of said felloe probe manipulator.

14. The flaw detection machine of claim 13, wherein,
said first jacking mechanism, said second jacking mechanism and said telescopic mechanism are an electric cylinder, an oil cylinder or an air cylinder.

15. The flaw detection machine of claim 1, comprising
two said tread probe frames, respectively provided at both ends of said tread probe manipulator.

* * * * *